(12) United States Patent
Ashton et al.

(10) Patent No.: US 7,314,967 B2
(45) Date of Patent: Jan. 1, 2008

(54) MOISTURE RESPONSIVE SEALING MEMBERS IN DISPOSABLE ABSORBENT ARTICLES

(75) Inventors: Gregory Ashton, Cincinnati, OH (US); Eiro Fukuda, Mason, OH (US); Donald Louis Zgoda, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 96 days.

(21) Appl. No.: 10/854,062

(22) Filed: May 26, 2004

(65) Prior Publication Data

US 2005/0267428 A1    Dec. 1, 2005

(51) Int. Cl.
*A61F 13/15* (2006.01)

(52) U.S. Cl. .......... 604/368; 604/385.12; 604/385.101; 604/385.04; 604/385.25; 604/385.29; 604/373; 604/369

(58) Field of Classification Search ................ 604/368, 604/385.12, 385.101, 385.04, 385.25, 385.29, 604/373, 369
See application file for complete search history.

(56) References Cited

U.S. PATENT DOCUMENTS

| | | |
|---|---|---|
| 3,860,003 A | 1/1975 | Buell |
| 3,911,173 A | 10/1975 | Sprague, Jr. |
| 3,929,135 A | 12/1975 | Thompson |
| 4,246,900 A | 1/1981 | Schröder |
| 4,324,246 A | 4/1982 | Mullane et al. |
| 4,342,314 A | 8/1982 | Radel et al. |
| 4,430,086 A | 2/1984 | Repke |
| 4,463,045 A | 7/1984 | Ahr et al. |
| 4,496,360 A | 1/1985 | Joffe et al. |
| 4,557,777 A * | 12/1985 | Sabee ................ 156/201 |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,743,246 A | 5/1988 | Lawson |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,888,231 A | 12/1989 | Angstadt |
| 4,892,536 A | 1/1990 | DesMarais et al. |

(Continued)

FOREIGN PATENT DOCUMENTS

EP     0 219 326 A2     4/1987

(Continued)

*Primary Examiner*—Tatyana Zalukaeva
*Assistant Examiner*—Ginger Chapman
(74) *Attorney, Agent, or Firm*—Jay A. Krebs; George H. Leal; John G. Powell

(57) ABSTRACT

Moisture responsive members are disposed outboard of the absorbent core within disposable absorbent articles. The moisture responsive members expand in response to moisture from the wearer of the absorbent article thereby creating a seal between the moisture responsive member and the wearer of the absorbent article. The moisture responsive members can be disposed along the longitudinal sides of the disposable absorbent article or along the waist edges, both front and rear, of the disposable absorbent article.

18 Claims, 8 Drawing Sheets

U.S. PATENT DOCUMENTS

| | | | |
|---|---|---|---|
| 4,909,803 A | 3/1990 | Aziz et al. | |
| 4,988,344 A | 1/1991 | Reising et al. | |
| 4,990,147 A | 2/1991 | Freeland | |
| 4,998,929 A | 3/1991 | Bjorksund et al. | |
| 5,006,394 A | 4/1991 | Baird | |
| 5,037,416 A | 8/1991 | Allen et al. | |
| 5,064,421 A * | 11/1991 | Tracy | 604/385.21 |
| 5,087,506 A * | 2/1992 | Palumbo | 428/194 |
| 5,102,597 A | 4/1992 | Roe et al. | |
| 5,124,188 A | 6/1992 | Roe et al. | |
| 5,137,537 A | 8/1992 | Herron et al. | |
| 5,147,345 A | 9/1992 | Young et al. | |
| 5,260,345 A | 11/1993 | DesMarais et al. | |
| 5,269,775 A | 12/1993 | Freeland et al. | |
| 5,324,561 A | 6/1994 | Rezai et al. | |
| 5,342,338 A | 8/1994 | Roe | |
| 5,372,766 A | 12/1994 | Roe | |
| 5,387,207 A | 2/1995 | Dyer et al. | |
| 5,428,076 A | 6/1995 | Roe | |
| 5,518,801 A | 5/1996 | Chappell et al. | |
| 5,522,809 A * | 6/1996 | Larsonneur | 604/361 |
| 5,536,264 A | 7/1996 | Hsueh et al. | |
| 5,571,096 A | 11/1996 | Dobrin et al. | |
| 5,575,785 A | 11/1996 | Gryskiewicz et al. | |
| 5,607,760 A | 3/1997 | Roe | |
| 5,609,587 A | 3/1997 | Roe | |
| 5,635,191 A | 6/1997 | Roe et al. | |
| H1670 H | 7/1997 | Aziz et al. | |
| 5,643,588 A | 7/1997 | Roe et al. | |
| 5,649,918 A | 7/1997 | Schleinz | |
| 5,650,222 A | 7/1997 | DesMarais et al. | |
| 5,766,213 A | 6/1998 | Hackman et al. | |
| 5,797,824 A * | 8/1998 | Tracy | 604/385.29 |
| 5,865,823 A | 2/1999 | Curro | |
| 5,935,118 A | 8/1999 | Gryskiewicz et al. | |
| 5,938,648 A | 8/1999 | LaVon et al. | |
| 5,947,949 A | 9/1999 | Inoue et al. | |
| 5,968,025 A | 10/1999 | Roe et al. | |
| 5,997,520 A | 12/1999 | Ahr et al. | |
| 6,068,924 A | 5/2000 | Palumbo | |
| 6,110,050 A | 8/2000 | Tammera | |
| 6,121,509 A | 9/2000 | Ashraf et al. | |
| 6,149,636 A | 11/2000 | Roe et al. | |
| 6,160,198 A | 12/2000 | Roe et al. | |
| 6,180,847 B1 | 1/2001 | Ahr et al. | |
| 6,186,991 B1 | 2/2001 | Roe et al. | |
| 6,224,961 B1 | 5/2001 | Hsueh et al. | |
| 6,232,520 B1 | 5/2001 | Hird et al. | |
| 6,258,996 B1 | 7/2001 | Goldman | |
| 6,296,929 B1 * | 10/2001 | Gentile et al. | 428/218 |
| 6,420,627 B1 | 7/2002 | Ohnishi et al. | |
| 6,441,266 B1 | 8/2002 | Dyer et al. | |
| 6,455,753 B1 | 9/2002 | Glaug et al. | |
| 6,476,104 B1 | 11/2002 | Nakamura et al. | |
| 6,506,958 B2 * | 1/2003 | Williams | 604/361 |
| 6,551,292 B1 | 4/2003 | D'Acchioli et al. | |
| 6,566,578 B1 | 5/2003 | Glaug et al. | |
| 6,706,029 B1 | 3/2004 | Suzuki et al. | |
| 6,794,557 B1 | 9/2004 | Klemp et al. | |
| 2003/0054342 A1 | 3/2003 | Star et al. | |
| 2003/0114810 A1 | 6/2003 | Weber | |
| 2003/0125689 A1 | 7/2003 | Olson et al. | |
| 2003/0139713 A1 | 7/2003 | Olson et al. | |
| 2003/0208171 A1 | 11/2003 | Zehner et al. | |
| 2005/0043696 A1 | 2/2005 | Schmidt et al. | |
| 2005/0101928 A1 | 5/2005 | Beruda et al. | |

FOREIGN PATENT DOCUMENTS

| | | |
|---|---|---|
| EP | 0 804 914 A1 | 5/1997 |
| EP | 0 947 549 A1 | 10/1999 |
| EP | 0 752 892 B1 | 7/2001 |
| EP | 0 808 146 B1 | 12/2001 |
| EP | 1 005 309 B1 | 7/2002 |
| JP | 05-293135 | 11/1993 |
| JP | 8-196566 | 8/1996 |
| JP | 8-196567 | 8/1996 |
| WO | WO 95/16746 A1 | 6/1995 |
| WO | WO 95/24173 A2 | 9/1995 |
| WO | WO 00/03670 A1 | 1/2000 |
| WO | WO 01/05440 A2 | 1/2001 |
| WO | WO 01/35889 A1 | 5/2001 |
| WO | WO 03/051247 A2 | 6/2003 |
| WO | WO 2004/030592 A1 | 4/2004 |

* cited by examiner

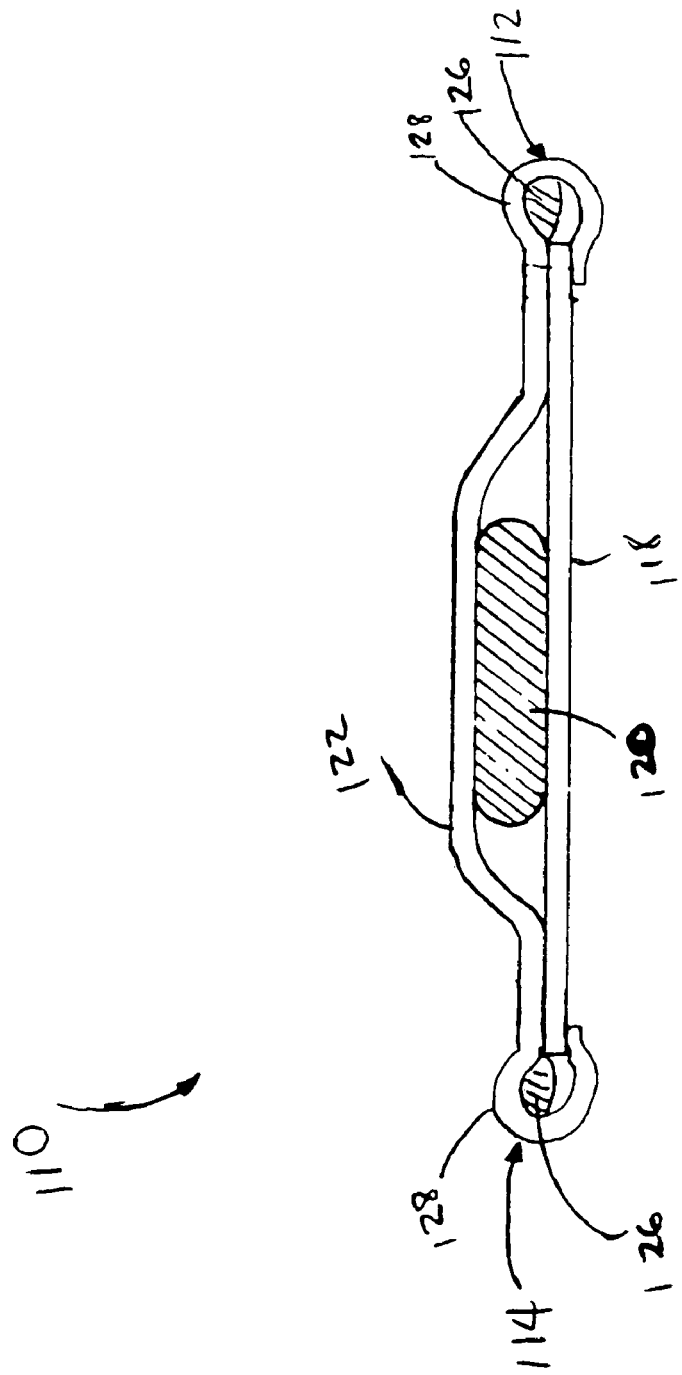

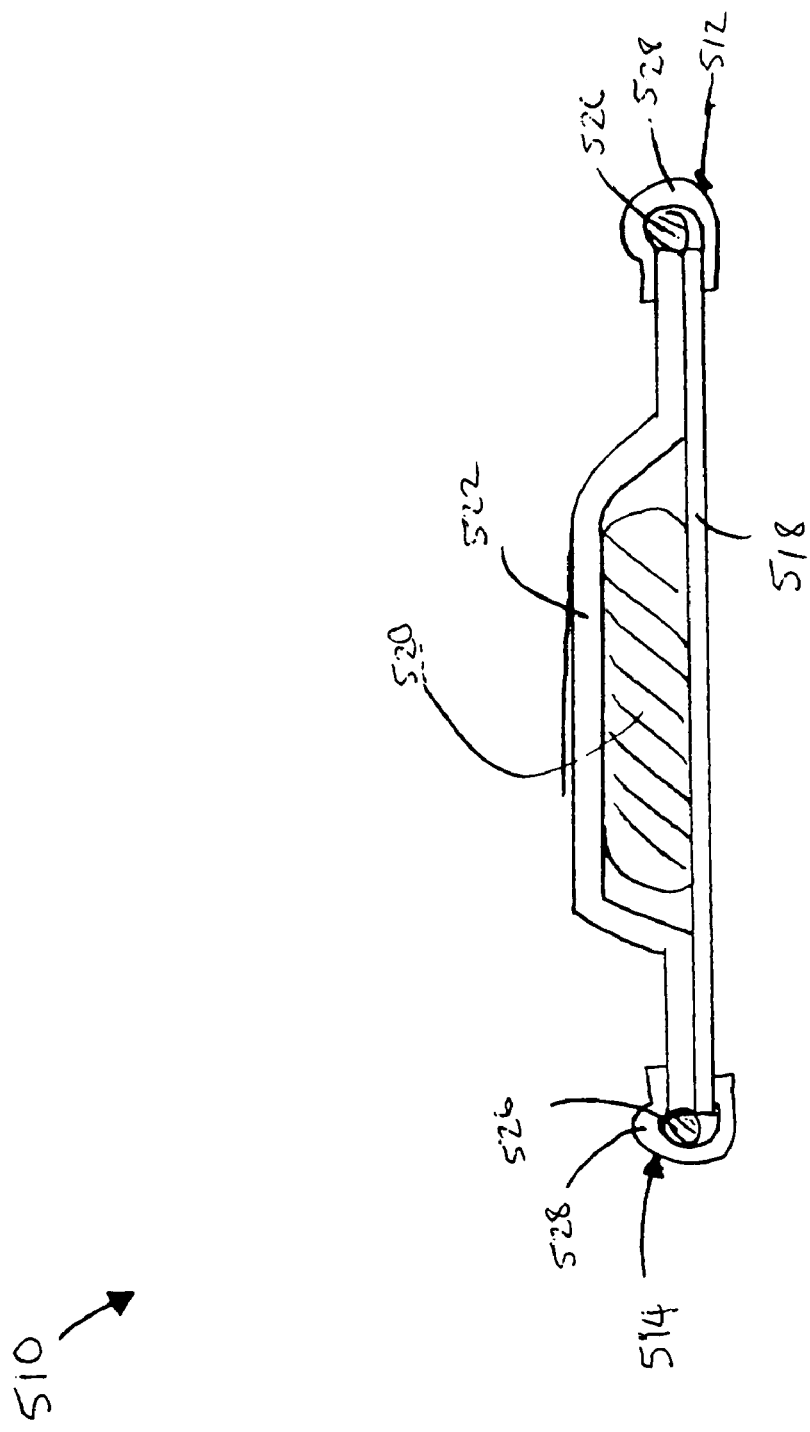

MOISTURE RESPONSIVE SEALING MEMBERS IN DISPOSABLE ABSORBENT ARTICLES

FIELD OF THE INVENTION

The present invention relates to disposable absorbent articles such as diapers, incontinent briefs, training pants, cataminial products, and the like and more particularly, to absorbent articles having moisture responsive sealing features which provide more effective leakage protection for the absorbent article and more comfort for the wearer of the absorbent article.

BACKGROUND OF THE INVENTION

Infants and other incontinent individuals wear absorbent articles such as diapers to receive and contain urine and other body exudates. In general, absorbent articles function both to contain the discharged materials and to isolate these materials from the body of the wearer and from the wearer's garments and bed clothing. However, in some instances, particularly absorbent articles used for potty training, the absorbent article may be designed such that the discharged materials, specifically urine, are not isolated from the body of the wearer. Regardless of whether the discharged materials are isolated from the wearer's body, it is important to completely eliminate or at least minimize leakage from the absorbent article.

In an effort to control leakage from absorbent articles, many improvements have been made in the field of elastics and elastic like materials. Despite these improvements, absorbent articles still have a tendency to sag or gap away from the body of the wearer during wear. This sagging/gapping is caused by the relative motions of the wearer as the wearer breathes, moves and changes positions, by the downward forces generated when the absorbent article is loaded with exudates, and by the deformation of the materials of the absorbent article itself when subjected to such wearer's motions. This sagging/gapping of the absorbent article can lead to premature leakage and poor fit of the absorbent article about the wearer in the waist regions and the leg regions of the absorbent article.

In order to more snugly fit absorbent articles about the waist of the wearer, certain commercially available absorbent articles have been provided with elastic waist features. Elastic waist features will typically comprise an elasticized waistband consisting of an elastic member contractibly affixed between the topsheet and the backsheet. The elasticized waistband is designed to expand and contract with the wearer's motions and to maintain the fit of the absorbent article about the waist of the wearer during use. However, it has been found that absorbent articles having elastic waist features also have a tendency to sag/gap and slide/slip during use. Further, the elastic waist feature has a tendency to rollover or roll-in at the front of the diaper resulting in a lack of fit about the waist of the wearer.

Similarly, leg elastics have been utilized in absorbent articles to try to preclude leakage about the legs of the wearer. However, leg elastics have not sufficiently reduced the amount of leakage in absorbent articles, and, in particular, leakage has been an issue in absorbent articles which include an absorbent core of a narrow crotch width. The leg elastics can be tensioned in order to maximize the leakage performance of the leg elastics; however, tensioning of the leg elastics tends to reduce the natural convection within the absorbent article. As the natural convection decreases, the relative humidity within the absorbent article increases. This increase in relative humidity in turn increases the chances of redmarking the wearer's skin.

The addition of containment flaps has also been utilized to help reduce leakage, but such absorbent articles have still had an undesirable amount of leakage. The containment flaps are often equipped with high tension elastics in order to maintain contact with the wearer's skin. As a consequence of the high tension elastics, a higher localized pressure against the skin of the wearer is created which increases the likelihood of redmarking the wearer's skin. Unfortunately, the problem of redmarking is often exacerbated by the movement of the wearer, because the skin of the wearer moves relative to the high tension elastics. Also, because the high tension elastics increase the friction between the wearer's skin and the high tension elastics, the likelihood and severity of abrasion to the skin as well as the likelihood and severity of redmarking is increased.

Therefore, there exists a need for an absorbent article to have improved leakage characteristics under compressive forces with consideration given to the movements of the wearer. There is a need for an absorbent article that reacts to the wearer and can provide maximum leakage protection when the leakage protection is needed the most. Also, the absorbent article should provide this protection while maximizing the comfort to the wearer.

SUMMARY OF THE INVENTION

The present invention pertains to a disposable absorbent article having a first longitudinal edge, a second longitudinal edge, a front waist edge, and a rear waist edge. The disposable article also comprises a backsheet, a topsheet that is bonded to the backsheet, and an absorbent core disposed between the topsheet and the backsheet. Also, the disposable absorbent article further comprises a moisture responsive member(s) attached to the disposable absorbent article outboard of the absorbent core, along the first longitudinal edge, or the second longitudinal edge, or proximate to the front waist edge, or proximate to the rear waist edge of the disposable absorbent article. The moisture responsive member provides contact with a portion of a wearer's body such that when the moisture responsive member is wetted by moisture from the wearer's body, the moisture responsive member expands against the portion of the wearer's body to form a seal between the moisture responsive member and the portion of the wearer's body.

A moisture responsive member may comprise a liquid permeable sheath which substantially encloses a super absorbent material. Moisture from the wearer permeates the liquid permeable sheath and causes the super absorbent material to expand. Upon expansion of the super absorbent material, the formation of the seal between the moisture responsive member and the portion of the wearer's body is created.

The disposable absorbent article may comprise a chassis having a waist opening, a first leg opening, a second leg opening, a front waist edge and a rear waist edge, a front waist region and a rear waist region adjacent to the respective front and rear waist edges, and a crotch region intermediate the front and rear waist regions. The disposable absorbent article may further comprise a topsheet, at least partially bonded to a backsheet, an absorbent core disposed in the crotch region intermediate the topsheet and the backsheet. Also, the absorbent article may comprise a first seal member joined to the disposable absorbent article along the first leg opening and a second seal member joined to the disposable absorbent article along the second leg opening. The first and second seal members expand when wetted by moisture from a wearer's body thereby decreasing the size of the first leg opening and the second leg opening, which in turn, creates a seal between the first seal member and the wearer's body and the second seal member and the wearer's body.

BRIEF DESCRIPTION OF THE DRAWINGS

FIG. 2A is a cross sectional view of the disposable diaper with an alternate embodiment of the present invention incorporated therein.

FIG. 5 is a cross sectional view of a cataminial structure with the present invention incorporated therein.

DETAILED DESCRIPTION OF THE INVENTION

Figure 1:
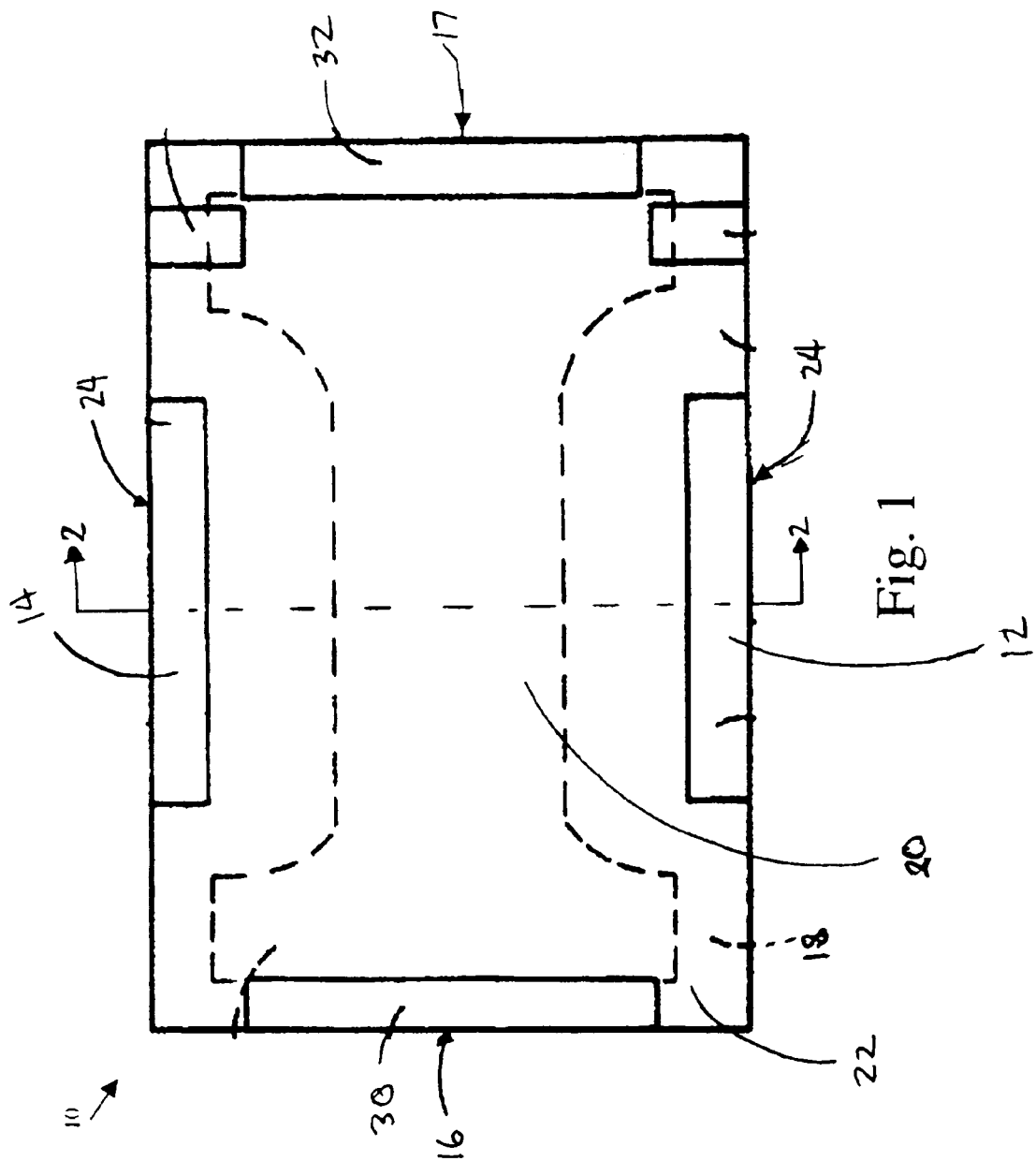
FIG. 1 is a view of a disposable diaper in a flattened state with the present invention incorporated therein.

Definitions:

As used herein, the following terms have the following meanings:

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 10, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

"Longitudinal" is a direction running parallel to the maximum linear dimension of the article and includes directions within ±45° of the longitudinal direction.

The "lateral" or "transverse" direction is orthogonal to the longitudinal direction.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The terms "permeable" and "impermeable" refer to the penetrability of materials in the context of the intended usage of disposable absorbent articles. Specifically, the term "permeable" refers to a layer or a layered structure having pores or openings that permit liquid water to pass through its thickness in the absence of a forcing pressure. Conversely, the term "impermeable" refers to a layer or a layered structure through the thickness of which liquid water cannot pass in the absence of a forcing pressure. As is well known in the art, a common method for measuring the permeability of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "retard" and "flow control layer" refer to the fact that different layers or layered structures may be permeable while differing in the flow rates at which they permit liquid water to pass through their respective thicknesses. For example, a layer containing capillary channels and through whose thickness liquid water wicks in the absence of any forcing pressure is considered to be permeable. However, the flow rate at which liquid water can pass through the thickness of such a layer may be lower than the flow rate at which liquid water can pass through the thickness of a layer containing holes that are too large to act as capillary channels. Similarly, two layers both containing capillary channels and through whose thicknesses liquid water wicks in the absence of any forcing pressure are both considered to be permeable. However, the capillary channels in one of the layers may differ in size from those in the other layer or may be more numerous than those in the other layer, such that the wicking flow rate of liquid water through the one layer may be greater than that through the other layer. Thus, in a layered structure, one layer serving as a flow control layer may retard the passage of liquid water, and likewise of bodily wastes that are aqueous in nature, through the thickness of the layered structure, relative to the flow rate at which another of the layers in the layered structure would permit the passage of the liquid water through its thickness in the absence of the flow control layer.

As used herein the term "wet" is used to refer to the act of providing moisture to an element of the claimed invention. In this instance, moisture from the wearer wets, i.e. provides moisture to, the moisture responsive member thereby causing the moisture responsive member to expand.

As used herein the term "moisture" is used to refer to either liquid or vapor or a combination thereof of urine, sweat, blood, fecal material, or any other body exudate which comprises either liquid or vapor.

The present invention may be incorporated into disposable absorbent articles in a variety of ways. The following figures are merely examples of such incorporation and are not meant to be illustrative of the sole methods for implementation of the present invention into a disposable absorbent article. For instance, FIG. 1 shows a disposable diaper 10 with a front waist edge 16, a rear waist edge 17 and longitudinal edges 24. The disposable diaper 10 may incorporate moisture responsive members in the form of first and second seal members 12 and 14, respectively, attached to the disposable diaper 10 along the longitudinal edges 24. Alternatively, the disposable diaper 10 may incorporate moisture responsive members in the form of a front waist seal member 30 that is disposed near the front waist edge 16 or a rear waist seal member 32 that is disposed near the rear waist edge 17. Both the front waist seal member 30 and the rear waist seal member 32 can be used in conjunction with the first and second seal members 12 and 14, respectively, or individually. Similarly, the front waist seal member 30 may be used in conjunction with the rear waist seal member 32, or they may be incorporated into the absorbent article individually.

As an example of the operation of the present invention, the moisture responsive members expand upon absorbing moisture from the wearer. For example, in the case of liquid urine, the urine wicks through the topsheet of the absorbent article and wets the moisture responsive member. Upon absorbing moisture from the wearer, the moisture responsive member reacts by expanding. If the moisture responsive members are the first and second seal members 12 and 14, the expansion is against and about the legs of the wearer. Conversely, if the moisture responsive members are the front waist seal member 30 or the rear waist seal member 32, the expansion is against the front waist area and rear waist area of the wearer, respectively.

As the moisture responsive members expand, the surface area of the moisture responsive member increases, thereby decreasing the localized pressure exerted against the skin of the wearer. This in turn decreases the likelihood of redmarking the wearer's skin. Also, because the moisture responsive member expands, leaks from the absorbent article are minimized.

In addition, because the moisture responsive members can absorb moisture vapor, the moisture responsive members can decrease the relative humidity within the absorbent article thereby providing the wearer with a more comfortable wearing experience. Note that all embodiments discussed herein operate in a similar fashion as discussed above, i.e. moisture from the wearer wets the moisture responsive member and the moisture responsive member expands against the wearer to create a seal between the moisture responsive member and the wearer.

Figure 2:
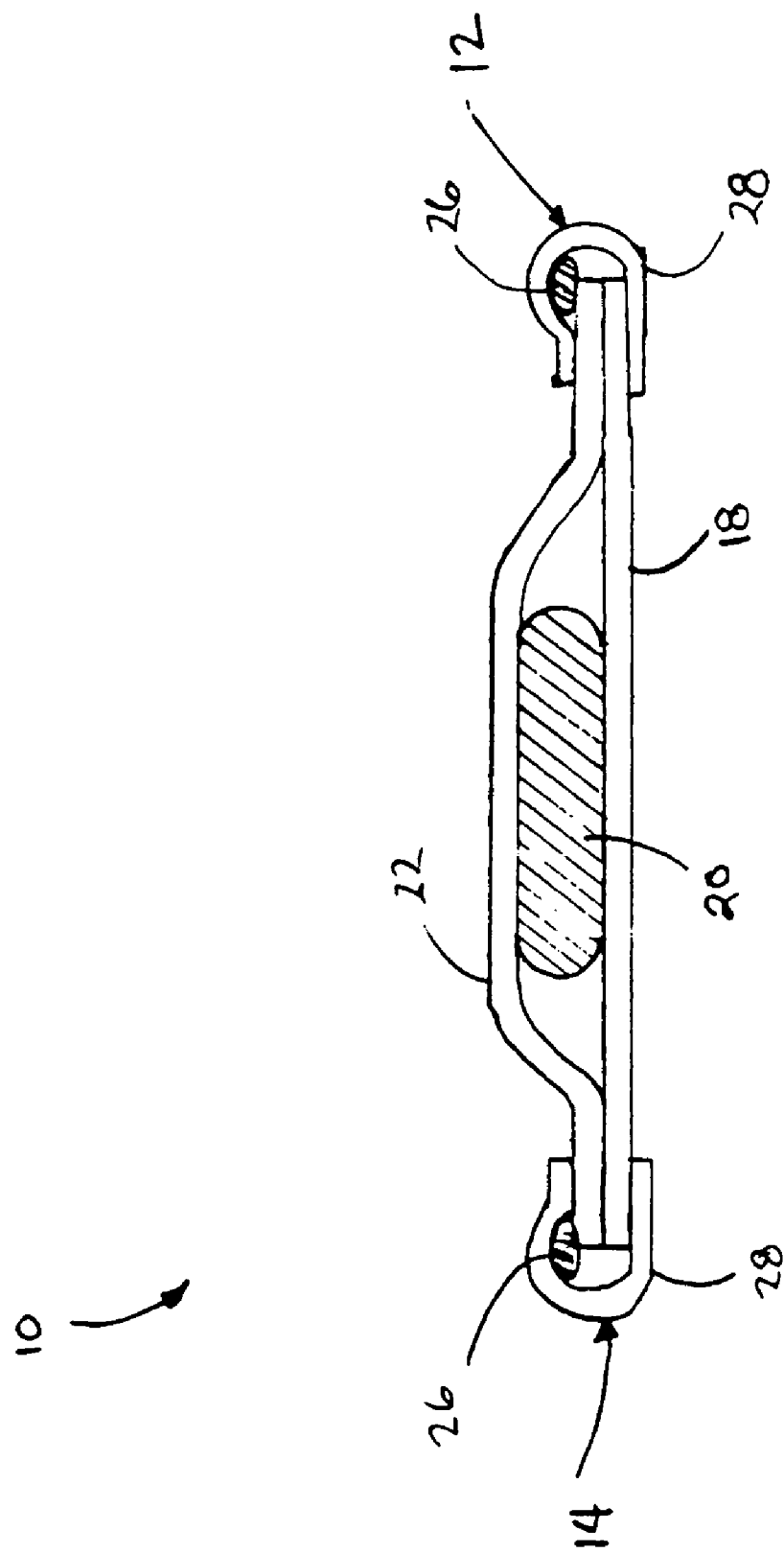
FIG. 2 is a cross sectional view of the disposable diaper with the present invention incorporated therein.

Regarding FIG. 2, the disposable absorbent article 10 has a backsheet 18 with a topsheet 22 joined thereto and an absorbent core 20 disposed in between the topsheet 22 and the backsheet 18. The first and second seal members 12 and 14, respectively, are disposed along longitudinal edges 24 (See FIG. 1) outboard of the absorbent core 20. Although not shown in FIG. 2, the front waist seal member 30, and the rear waist seal member 32 (See FIG. 1) include an super absorbent material 26 positioned inside a liquid permeable sheath 28.

Figure 2B:
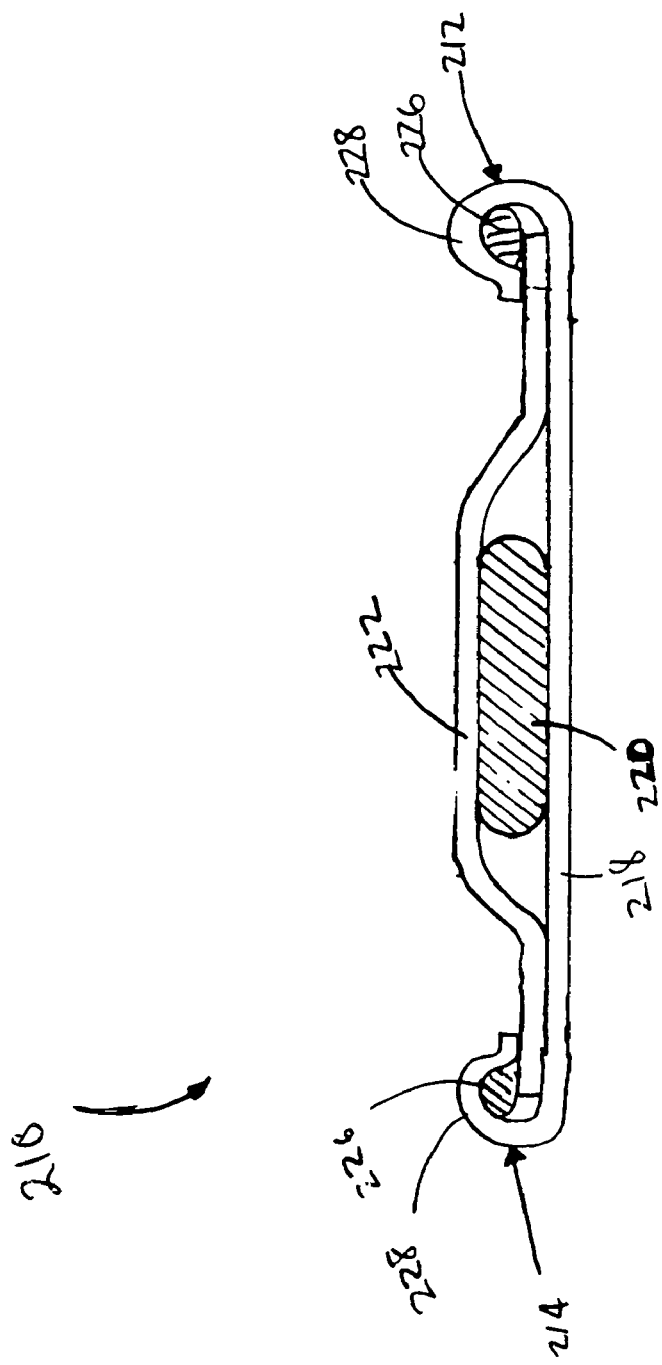
FIG. 2B is a cross sectional view of the disposable diaper with an alternate embodiment of the present invention incorporated therein.

The liquid permeable sheath 28 can be joined along the edges of the topsheet 22 and backsheet 18. The liquid permeable sheath 28 should be joined to the disposable absorbent article 10 such that the super absorbent material 26 is substantially enclosed by the liquid permeable sheath 28. However, the liquid permeable sheath 28 should substantially enclose the super absorbent material 26 without inhibiting the moisture of the wearer from wetting the super absorbent material 26. Alternatively, the liquid impermeable sheath may comprise a topsheet 122 (See FIG. 2A) or a backsheet 218 (See FIG. 2B). Note that for any embodiments discussed herein, the attachment of the liquid permeable sheath 28 to the disposable absorbent article should not inhibit moisture of the wearer from wetting the super absorbent material 26.

Figure 2C:
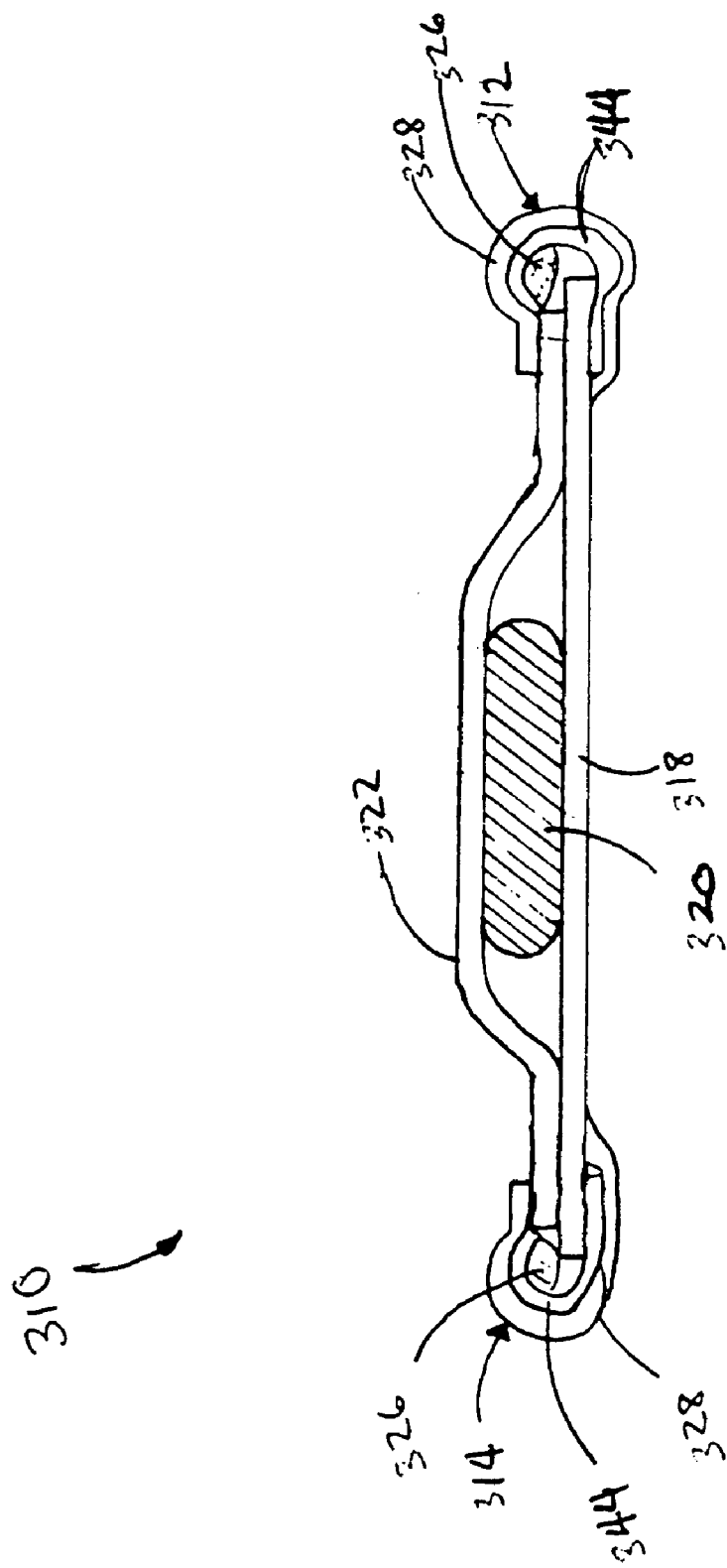
FIG. 2C is a cross sectional view of the disposable diaper with an alternate embodiment of the present invention incorporated therein.

FIG. 2C shows a liquid impermeable layer 344 enclosed within a liquid permeable sheath 328. Although not shown in FIG. 2C, the liquid impermeable layer 344 can be implemented without the liquid permeable sheath 328. The purpose of the liquid impermeable layer 344 would be to preclude or minimize the leakage of wetted super absorbent material 326 outside the liquid permeable sheath 328 or to preclude the wetted super absorbent material 326 from getting on the wearer. The liquid impermeable layer 344 can be positioned inside the liquid permeable sheath 328 (as shown in FIG. 2C) or outside the liquid permeable sheath 328. However, the liquid impermeable layer 344 must be positioned such that the liquid impermeable layer 344 does not inhibit the moisture of the wearer from wetting the super absorbent material 326. Thus, the liquid impermeable layer 344 can be equipped with slots or openings or any means known in the art for allowing moisture to penetrate through an otherwise liquid impermeable layer.

A liquid impermeable layer may comprise an elastomeric material which includes those materials manufactured by Kraton Polymers Inc. of Houston, Tex. and sold under trade names Kraton D and Kraton G. For the purposes of the present invention, any suitable liquid impermeable material known in the art may be used. However, if the backsheet 318 is used as the liquid permeable sheath 328, then the need for the liquid impermeable layer 344 (See FIG. 2C) may be obviated if the backsheet comprises a liquid impermeable film.

Figure 3:
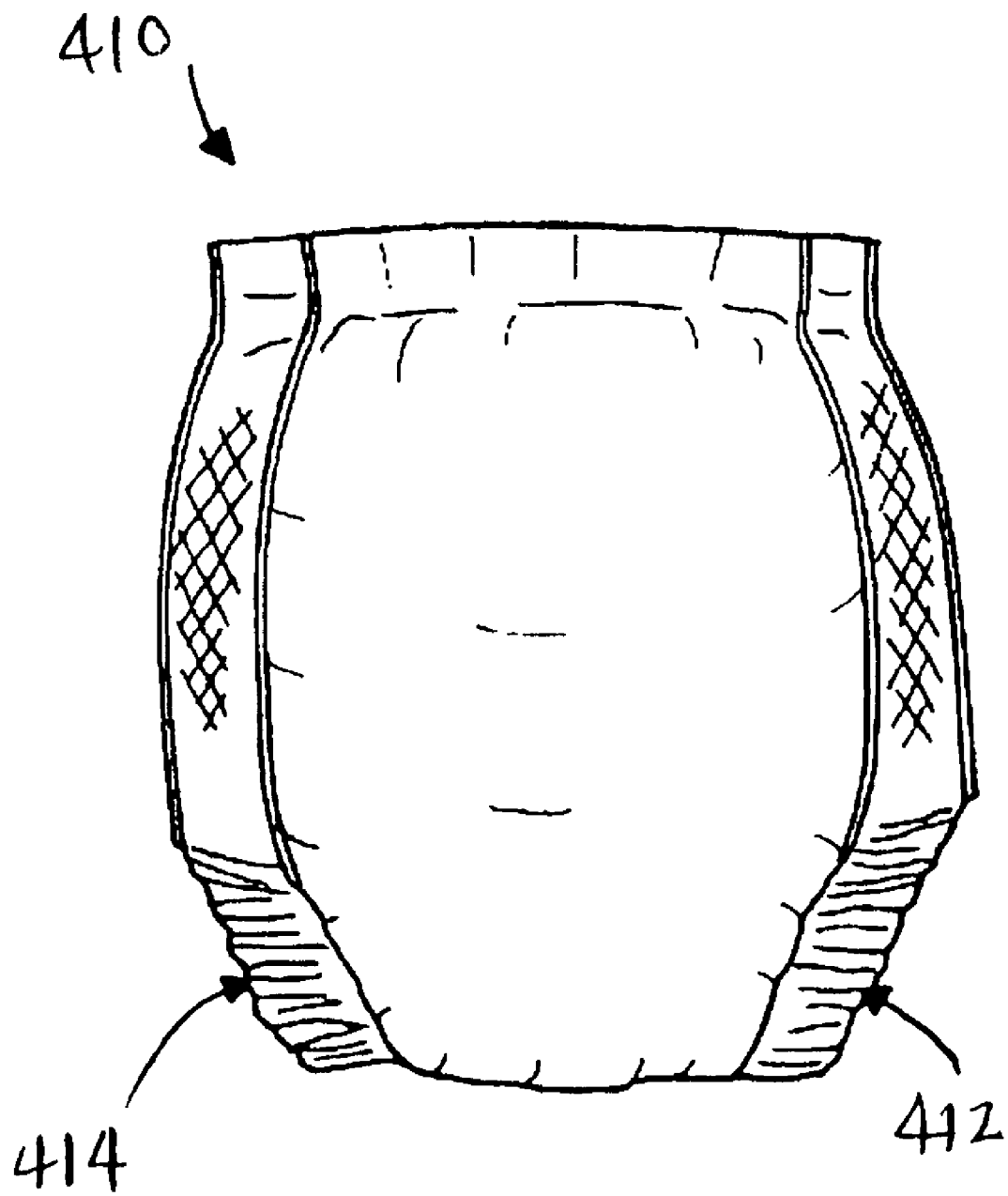
FIG. 3 is a view of the present invention incorporated into a training pant like structure.

The present invention may also be incorporated into a training pant like structure as shown in FIG. 3. In this embodiment of the present invention, the first seal member 412 and second seal member 414 are positioned in the disposable absorbent article 410 such that they contact the legs of the wearer.

Figure 4:
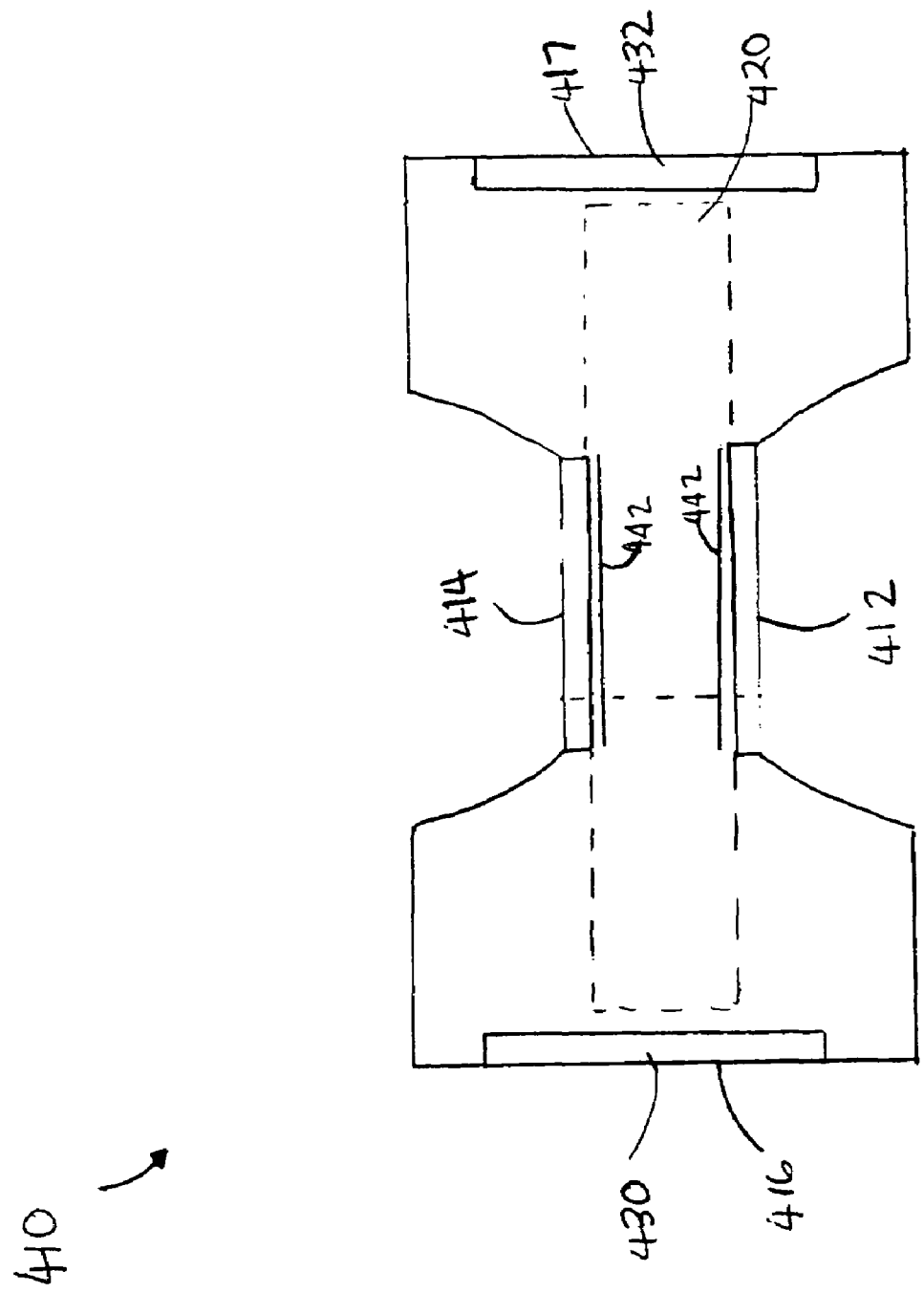
FIG. 4 is a view of the pant like structure, in a flattened state, showing the present invention implemented therein.

In an alternative embodiment, the disposable absorbent article 410 (See FIG. 4) may further comprise a front waist seal member 430 that is disposed along the front waist edge 416. The disposable absorbent article 410 may comprise, in conjunction with the front waist seal member 430 or on its own, a rear waist seal member 432 that is disposed along the rear waist edge 417. Also, the disposable absorbent article 410 may further comprise barrier leg cuffs 442 disposed inboard of the first seal member 412 and the second seal member 414.

Any embodiment discussed herein preferably further includes leg cuffs which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

The present invention may be incorporated into absorbent articles such as catamenial products in any manner discussed herein. As shown in FIG. 5, cataminial product 510 could incorporate the present invention via the first and second seal members 512 and 514, respectively. In this instance, the moisture of the wearer wicks through the topsheet 522 and wets the super absorbent material 526 which is substantially enclosed by the liquid permeable sheath 528.

Although not shown in the figures, the absorbent article may incorporate the use of air inflated members such that a snug fit is initially sustained. The air inflated members can be pre-inflated such that a snug fit is immediately established upon placement of the absorbent article on the wearer. Also, the air inflated members may be adjustable such that a consumer may add or remove air via a pumping means or an air release means, respectively. For instance, the consumer can add air to an air inflated member such that the air inflated member expands and provides for better protection against leakage while also minimizing the localized pressure exerted against the wearer by the air inflated member. For the purposes of adding air to the air inflated members, any pumping means known in the art can be used. For the purposes of removing air from the air inflated members, any air releasing means known in the art may be used.

Alternatively, or in conjunction with the air inflated members, the absorbent article may further incorporate the use of an elastomeric material in order to initially sustain the fit of the disposable absorbent article to the wearer. So, the moisture responsive members either in the leg area, i.e. the first seal member or the second seal member, or the front waist seal member or the rear waist seal member may incorporate an elastomeric material in order to sustain the initial fit of the absorbent article to the wearer. Also, the moisture responsive members may be sized or pre-expanded such that a snug fit exists prior to the wetting of the moisture responsive members by the wearer. However, if an elastomeric liquid impermeable material is used for the liquid impermeable layer, as discussed previously, the need for an additional elastomeric material to be incorporated into the moisture responsive members may be obviated. If an elastomeric material is still needed, then any suitable elastomeric material known in the art may be used to make an elastic leg cuff or an elastic waistband of the disposable absorbent article.

Along with providing the absorbent article with the initial fit to the wearer, the elastomeric material may further provide gathers to the liquid permeable layer such that when the super absorbent material expands, the liquid permeable layer can accommodate the expansion of the super absorbent material. Alternatively or in conjunction with the elastomeric material, the liquid permeable layer can expand to accommodate the expansion of the super absorbent material.

In general, the super absorbent material within the moisture responsive members should be evenly distributed within the liquid permeable sheath. However, the super absorbent material may be perforated in order to increase the permeability of the moisture responsive member thereby making the moisture responsive member more sensitive to moisture. Moreover, the super absorbent material may be strategically placed in the liquid permeable sheath and allowed to expand into areas of the liquid permeable sheath which were not initially supplied with any super absorbent material.

The liquid permeable sheath referred to herein can be a nonwoven material and may comprise: natural fibers, such as wood pulp fibers, cotton, rayon (also known as viscose) and combinations thereof; synthetic fibers, such as polyolefins, polyesters, and combinations thereof; and combinations thereof. The liquid permeable sheath may be formed in any conventional fashion, such as but not limited to, hydroentangling, carded, meltblown, airlaid and the like, and combinations thereof.

The liquid permeable sheath may be extensible or non-extensible and may comprise a woven or nonwoven material. Any suitable permeable material known in the art may be used as the liquid permeable sheath. As an example, the liquid permeable sheath can be a carded nonwoven material. In this instance, the liquid permeable sheath can be made of bi-component fibers of a polyethylene (PE) and a polypropylene (PP) where the ratio of PE/PP is about 50/50. A suitable carded nonwoven web having a ratio of PE/PP of about 50/50 is obtainable from Chisso Corp., Moriyama, Japan.

Alternatively, the liquid permeable sheath may be a spunbonded nonwoven material, an example of which is obtainable from Mitsui Petrochemical Industries, Ltd., Tokyo, Japan. The liquid permeable sheath may be made of bi-component fibers of a polyethylene (PE) and a polypropylene (PP). The ratio of PE/PP is about 80/20.

The topsheet referred to herein is preferably positioned the adjacent body surface of the absorbent core and may be joined thereto and/or to the backsheet by any attachment means known in the art. Suitable attachment means are described above with respect to means for joining the backsheet to other elements of the diaper. In one preferred embodiment of the present invention, the topsheet and the backsheet are joined directly to each other in some locations and are indirectly joined together in other locations by directly joining them to one or more other elements of the diaper.

The topsheet is preferably compliant, soft-feeling, and non-irritating to the wearer's skin. Further, at least a portion of the topsheet is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet can be found in U.S. Statutory Invention Registration No. H1670 published on Jul. 1, 1997 in the names of Aziz et al. Each of these references is hereby incorporated by reference herein. Alternatively, the topsheet may include an apertured web or film which is hydrophobic. This may be accomplished by eliminating the hydrophilizing treatment step from the production process and/or applying a hydrophobic treatment to the topsheet, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; and U.S. Pat. No. 5,968,025 entitled "Absorbent Article Having a Lotioned Topsheet" issued to Roe et al. on Oct. 19, 1999. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet, the backsheet or any portion of the topsheet or backsheet may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the aperture should have an area of between about 10 $cm^2$ and about 50 $cm^2$. The aperture 80 preferably has an area of between about 15 $cm^2$ and 35 $cm^2$.

Further, the topsheet may be fully or partially elasticated or may be foreshortened so as to provide a void space between the topsheet and the core. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core referred to herein may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No.

5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

Typically, absorbent cores are required to absorb and retain moisture, specifically urine, quickly and isolate the moisture from the wearer's body. However, particularly in training pants, an absorbent core is required to absorb urine or moisture more slowly. In doing so, the absorbent core allows the urine or moisture to contact the wearer's body. This provides the user with a wet sensation in the absorbent article which leads to improved potty training results. These types of absorbent cores, are referred to as training cores, and they typically have low or slow liquid acquisition properties. Any suitable training core known in the art can be used in conjunction with the present invention.

The backsheet referred to herein is generally that portion of the diaper positioned adjacent garment facing surface of the absorbent core which prevents the exudates absorbed and contained therein from soiling articles which may contact the diaper, such as bedsheets and undergarments. In preferred embodiments, the backsheet is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper while still preventing exudates from passing through the backsheet. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE., and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E.I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet may comprise elastomeric films, foams, strands, or combinations of these or other suitable materials with nonwovens or synthetic films.

The backsheet may be joined to the topsheet, the absorbent core or any other element of the diaper by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The super absorbent material discussed herein may comprise absorbent gelling material, Gelling Elastic Material produced by The Procter and Gamble Corp., Gelling Adhesive Material manufactured by H B Fuller of St. Paul, Minn. under the designation HydroLock, or superporous hydrogels manufactured by Akina West of Lafayette, Ind. under the designation Aquagel, fluid stable aggregates, or any combinations thereof.

The absorbent gelling material, hereinafter "AGM," include a variety of water-insoluble, but water-swellable polymers capable of absorbing large quantities of fluids. Such polymer materials are generally known in the art and include all those well-known polymers used or deemed useful in the context of disposable absorbent article technology. Particularly the AGMs disclosed in EP-A-752 892 or those disclosed in the textbook entitled "Modem Super Absorbent Technology" by F. L. Buchholz and A. T. Graham, published by Wiley VCH, New York, 1998 are useful in the context of the present invention.

The AGM particles may be of numerous shapes. The term "particles" refers to granules, fibers, flakes, spheres, powders, platelets, and other shapes and forms known to person skilled in the art of AGMs. The particles can be in the form of granules, beads, that have a particle size from about 10 µm to about 1000 µm, or even from about 100 µm to about 1000 µm, or even from about 150 µm to about 850 µm and or even from about 150 µm to about 500 µm. In another embodiment, the AGMs can be in the shape of fibers, i.e. elongated, acicular AGM particles. In another embodiment, the AGM may be pre-wetted such that the AGM is already in a gel like state. The fibers can also be in the form of a long filament that can be woven into a sheet. The AGM may be in sheet form and bonded to the liquid impermeable layer 44. The AGM may be printed or glued to the liquid impermeable layer using any suitable bonding or printing process that is well known in the art.

The fluid stable aggregates, hereinafter "FSA's," can be used to make up absorbent polymeric macrostructures. Exemplary FSA's structures for use in the moisture responsive members are described in U.S. Pat. No. 5,536,264 entitled "Absorbent Composites Comprising a Porous Macrostructure of Absorbent Gelling Particles and A Substrate" issued to Hsueh et al. on Jul. 16, 1996; U.S. Pat. No.

6,224,961 entitled "Absorbent Macrostructure Made From Mixtures of Different Hydrogel-Forming Absorbent Polymers for Improved Fluid Handling Capability" issued to Hsueh et al. on May 1, 2001; U.S. Pat. No. 5,428,076 entitled "Flexible, Porous, Absorbent, Polymeric Macrostructures and Methods of Making the Same" issued to Roe on Jun. 27, 1995; U.S. Pat. No. 5,372,766 entitled "Flexible, Porous, Absorbent, Polymeric Macrostructures and Methods of Making the Same" issued to Roe on Dec. 13, 1994; U.S. Pat. No. 5,324,561 entitled "Porous, Absorbent, Macrostructures of Bonded Particles Surface Crosslinked with Cationic Amino-Epichlorohydrin Adducts" issued to Rezai et al. on Jun. 28, 1994; U.S. Pat. No. 5,124,188 entitled "Porous, Absorbent, Polymeric Macrostructures and Methods of Making the Same" issued to Roe et al. on Jun. 23, 1992; and U.S. Pat. No. 5,102,597 entitled "Porous, Absorbent, Polymeric Macrostructures and Methods of Making the Same" issued to Roe et al. on Apr. 7, 1992. Each of these patent is incorporated by reference herein.

All documents cited in the Detailed Description of the Invention are, in relevant part, incorporated herein by reference. The citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having first longitudinal edge, a second longitudinal edge, a front waist edge, and a rear waist edge, the disposable article comprising:
   a backsheet;
   a topsheet bonded to the backsheet;
   an absorbent core disposed between the topsheet and the backsheet; and
   a first moisture responsive member attached to the disposable absorbent article along at least one of the first longitudinal edge, the second longitudinal edge, the front waist edge, and the rear waist edge of the disposable absorbent article outboard of the absorbent core, the moisture responsive member including an elastomeric material adapted to sustain the fit of the disposable absorbent article to the body of a wearer prior to the moisture responsive member being wetted by moisture from the body of the wearer wherein the first moisture responsive member provides contact with a portion of the wearer's body such that when the moisture responsive member is wetted by moisture from the wearer's body, the first moisture responsive member expands against the portion of the wearer's body to form a seal between the first moisture responsive member and the portion of the wearer's body.

2. The disposable absorbent article of claim 1, wherein the first moisture responsive member comprises an absorbent gelling material.

3. The disposable absorbent article of claim 2, wherein the absorbent gelling material is in a form comprising at least one of a gel, a sheet, a plurality of fibers, a powder, platelets, spheres, flakes, or granules.

4. The disposable absorbent article of claim 1, wherein the first moisture responsive member is joined to the disposable absorbent article proximate to the front waist edge or the rear waist edge of the disposable absorbent article.

5. The disposable absorbent article of claim 4, wherein the first moisture responsive member comprises an absorbent gelling material.

6. The disposable absorbent article of claim 4, wherein the first moisture responsive member comprises a super absorbent material.

7. The disposable absorbent article of claim 1 further comprising a second moisture responsive member, wherein the first moisture responsive member is joined to the disposable absorbent article proximate to the first longitudinal edge and the second moisture responsive member is joined to the disposable absorbent article proximate to the second longitudinal edge of the disposable absorbent article.

8. The disposable absorbent article of claim 7 wherein the first moisture responsive member and the second moisture responsive member comprise an absorbent gelling material.

9. The disposable absorbent article of claim 7, wherein the first moisture responsive member and the second moisture responsive member comprise a super absorbent material.

10. The disposable absorbent article of claim 7 further comprising a third moisture responsive member joined to the disposable absorbent article proximate to the front waist edge or the rear waist edge of the disposable absorbent article.

11. The disposable absorbent article of claim 10, wherein the first moisture responsive member, the second moisture responsive member, and the third moisture responsive member comprise an absorbent gelling material.

12. The disposable absorbent article of claim 10. wherein the first moisture responsive member, the second moisture responsive member, and the third moisture responsive member comprise a super absorbent material.

13. The disposable absorbent article of claim 10 wherein the third moisture responsive member is joined to the disposable absorbent article proximate to the front waist edge.

14. The disposable absorbent article of claim 13 further comprising a fourth moisture responsive member joined to the disposable absorbent article proximate to the rear waist edge of the disposable absorbent article.

15. The disposable absorbent article of claim 14, wherein the first moisture responsive member, the second moisture responsive member, the third moisture responsive member, and the fourth moisture responsive member comprise an absorbent gelling material.

16. The disposable absorbent article of claim 14, wherein the first moisture responsive member, the second moisture responsive member, the third moisture responsive member, and the fourth moisture responsive member comprise a super absorbent material.

17. The disposable absorbent article of claim 1, wherein the first moisture responsive member comprises a super absorbent material.

18. The disposable absorbent article of claim 17, wherein the super absorbent material comprises at least one of an absorbent gelling material, gelling elastic material, gelling adhesive material, superporous hydrogels, or any combination thereof.

* * * * *

UNITED STATES PATENT AND TRADEMARK OFFICE
CERTIFICATE OF CORRECTION

| | | |
|---|---|---|
| PATENT NO. | : 7,314,967 B2 | Page 1 of 1 |
| APPLICATION NO. | : 10/854062 | |
| DATED | : January 1, 2008 | |
| INVENTOR(S) | : Gregory Ashton et al. | |

It is certified that error appears in the above-identified patent and that said Letters Patent is hereby corrected as shown below:

<u>Column 12</u>
Line 41, delete "Modem" and insert --Modern--.

Signed and Sealed this

Seventeenth Day of June, 2008

JON W. DUDAS
*Director of the United States Patent and Trademark Office*